United States Patent
Arbuthnot et al.

(10) Patent No.: US 6,245,352 B1
(45) Date of Patent: Jun. 12, 2001

(54) PHARMACEUTICAL FORMULATION

(75) Inventors: Gordon Nelson Arbuthnot, Indianapolis, IN (US); Karen Klapper Lomas; Glenn Alan Meyer, both of Wilmington, NC (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/460,878

(22) Filed: Dec. 14, 1999

Related U.S. Application Data

(60) Provisional application No. 60/131,319, filed on Apr. 27, 1999.

(51) Int. Cl.$^7$ ............... A61K 9/20; A61K 9/14; A61K 9/16
(52) U.S. Cl. ............ 424/465; 424/464; 424/489; 424/493; 424/494
(58) Field of Search .................... 424/464, 465, 424/489, 493, 494

(56) References Cited

U.S. PATENT DOCUMENTS

| | | | |
|---|---|---|---|
| 5,874,418 | * | 2/1999 | Stella et al. ............ 514/58 |
| 5,942,248 | * | 8/1999 | Barnwell ............ 424/457 |

OTHER PUBLICATIONS

Italian Directory of Medicines, (OEMF spa, Via–Edolo–20125 Milano), NOLVADEX and NOLVADEX D, 1994.*
Physicians Desk Reference 50$^{th}$ Edition 1996, pp. 2842–2844, NOLVADEX, Published by Medial Economics Co., Montvale, N.J. 07645–1742.
FMC Corporation Trade Literature, Ac–Di–Sol, Croscarmellose Sodium, NF, SD–15 Updated 8/98, 11 pages. FMC Corporation Pharmaceutical Division, 1735 Market Street, Philadelphia, PA 19103.
De Vos, D., et al., *Meth. and Find. Exp. Clin. Pharmacol.,* 1989; 11(10):647–655.

* cited by examiner

Primary Examiner—Thurman K. Page
Assistant Examiner—S. Tran
(74) Attorney, Agent, or Firm—Gilbert V. Voy; Martin A. Hay

(57) ABSTRACT

The present invention relates to a pharmaceutical formulation, which comprises from 5 to 15% by weight of tamoxifen citrate and a first disintegrant which is croscarmellose sodium, the percentage by weight of croscarmellose sodium present in the formulation being chosen such that, in six 20 mg unit doses, an average of at least 65 percent by weight of the tamoxifen citrate in the formulation will dissolve within 10 minutes in 1000 mL of 0.02N hydrochloric acid at 37° C. when stirred at 100 rpm.

14 Claims, No Drawings

PHARMACEUTICAL FORMULATION

CROSS-REFERENCE

This application claims the benefit of U.S. Provisional Application No. 60/131,319, filed Apr. 27, 1999.

FIELD OF THE INVENTION

The present invention relates to a pharmaceutical formulation. More particularly, it relates to a new formulation of the compound tamoxifen citrate.

BACKGROUND OF THE INVENTION

Tamoxifen citrate is the non-proprietary name for the compound (Z)-2-[4-(1,2-diphenyl-1-butenyl)phenoxy]-N,N-dimethylethylamine 2-hydroxy-1,2,3-propanetricarboxylic acid. The compound is used in the treatment and prevention of breast cancer, and is believed to exert its anti-tumor effect through action as an anti-estrogen at estrogen binding sites in breast tissue. The compound and its preparation are described, for example, in U.S. Pat. No. 4,536,516.

Existing commercial formulations of tamoxifen citrate, such as NOLVADEX® (produced by Zeneca Pharmaceuticals, Wilmington Del., USA) and NOLVADEX® D (produced by Zeneca Limited, Macclesfield Cheshire, United Kingdom), contain 10 mg or 20 mg of the active ingredient, tamoxifen. Based on the results of clinical studies, it is believed that the optimum dose is 20 mg per day, which may be achieved by administering 10 mg tablets twice a day or a 20 mg tablet once a day.

Tamoxifen citrate is a compound with relatively poor solubility.

Formulations of a compound with relatively poor solubility can be relatively expensive to manufacture. Thus during manufacture, the dissolution rate of each batch of formulated compound must be tested against a dissolution specification to ensure consistency and compliance. Examples of such dissolution specifications are contained in the United States Pharmacopeia (USP) and the British Pharmacopoeia (BP). Batches that fail to pass the specification must be rejected. Formulations in which the dissolution rate of a compound is relatively close to the specification exhibit a relatively higher incidence of failed batches due to manufacturing variability. It is generally desirable to have a formulation that routinely passes the dissolution specification by a wide margin.

It is apparent that the compositions of the formulations of commercially available tamoxifen citrate vary around the world. For example, in the United States, NOLVADEX® 10 mg (produced by Zeneca Pharmaceuticals, Wilmington Del., USA) is reported in the U.S. Physicians Desk Reference, $50^{th}$ Edition 1996 (see above) to be formulated with carboxymethylcellulose calcium, magnesium stearate, mannitol and starch. In Europe, the Italian Directory of Medicines, 1994 (OEMF spa, Via Edolo- 20125 Milano) reports that NOLVADEX® D 20 mg (produced by Zeneca Limited, Macclesfield Cheshire, United Kingdom) contains tamoxifen citrate (30.4 mg), lactose (234 mg), starch (82.2 mg), gelatin (2.2 mg), croscarmellose sodium (7.2 mg), magnesium stearate (4.0 mg), hydroxypropylmethylcellulose (5.4 mg), polyethyleneglycol ("macrogol") (1.1 mg), and titanium dioxide (1.6 mg), the latter three ingredients presumably forming a coating for the tablet. The 10 mg formulation has half the weight of each ingredient.

BRIEF SUMMARY OF THE INVENTION

A new 20 mg tablet formulation of tamoxifen citrate has now been found which exhibits a much faster dissolution rate than either the commercial formulation of NOLVADEX® 20 mg in the USA or the commercial formulation of NOLVADEX® D 20 mg in Europe.

Accordingly, the present invention provides a pharmaceutical formulation, which comprises from 5 to 15% by weight of tamoxifen citrate and a first disintegrant which is croscarmellose sodium, the percentage by weight of croscarmellose sodium present in the formulation being chosen such that, in six 20 mg unit doses, an average of at least 65 percent by weight of the tamoxifen citrate in the formulation will dissolve within 10 minutes in 1000 mL of 0.02N hydrochloric acid at 37° C. when stirred at 100 rpm.

DETAILED DESCRIPTION OF THE INVENTION

The improved dissolution characteristics of the formulation according to the present invention are surprising, because NOLVADEX® 20 mg and NOLVADEX® D 20 mg have been found to exhibit essentially the same dissolution characteristics. Thus the presence of croscarmellose sodium in NOLVADEX® D 20 mg does not appear to confer any improved dissolution characteristics, when a comparison is made between NOLVADEX® 20 mg and NOLVADEX® D 20 mg.

The formulation may be in the form of a tablet or a capsule. Each tablet or capsule may contain, for example, 10 mg or 20 mg of tamoxifen in the form of tamoxifen citrate. Preferably it is in the form of a tablet, most preferably a 20 mg tablet.

It will be appreciated that the dissolution rate of tamoxifen citrate in a given formulation will differ according to whether the formulation is in the form of a tablet or a capsule, and depending upon how much tamoxifen citrate is present in each unit dose. For example, the tamoxifen citrate in a 10 mg tablet will dissolve faster than that in a 20 mg tablet of the same formulation.

A tablet may be un-coated or coated, for example with a conventional coating containing a colored dye, and may be of any shape, for example a disc.

As used in this specification, the term percentage by weight of an ingredient in the formulation refers to the percentage by weight of that ingredient based upon the total weight of the un-coated formulation. Thus, for example, in the Italian formulation of NOLVADEX® D 20 mg described hereinabove, the percentage by weight of croscarmellose sodium in the tablet formulation is 2%.

Preferably the percentage by weight of croscarmellose sodium present in the formulation is chosen such that at least 70 percent by weight of the tamoxifen citrate in the formulation will dissolve within 10 minutes, more preferably at least 75% by weight, especially at least 80% by weight.

The formulation preferably consists of an inter-granular component and an intra-granular component, said inter-granular component containing at least some of the croscarmellose sodium and the tamoxifen citrate. It will be appreciated that the presence of an inter-granular component and an intra-granular component results from the way in which the formulation is made, by granulating together the ingredients of the inter-granular component, and then mixing the granulated material so obtained with the ingredients of the intra-granulating material.

Preferably the inter-granular component further comprises from 5 to 15% by weight of a second disintegrant, from 55 to 75% by weight of a diluent and from 0.5 to 5% by weight of a binder, based upon the weight of the formulation.

The second disintegrant is preferably selected from starch and microcrystalline cellulose. Most preferably it is microcrystalline cellulose.

The diluent is preferably selected from lactose and mannitol. The mannitol may be powdered or granular. Preferably the mannitol is granular. It has been found that a higher percentage by weight of croscarmellose sodium may be required when powdered mannitol is used compared with when granular mannitol is used.

The binder is preferably selected from gelatin and polyvinylpyrrolidone. Most preferably it is polyvinylpyrrolidone.

The inter-granular component preferably contains from 0.75 to 2.5 percent by weight of croscarmellose sodium, based on the weight of the formulation.

Preferably the intra-granular component comprises from 5 to 15% by weight of a third disintegrant and from 0.5 to 1.5% by weight of a lubricant, based upon the total weight of the formulation.

The third disintegrant is preferably selected from starch and microcrystalline cellulose. Most preferably it is microcrystalline cellulose.

The lubricant is preferably magnesium stearate.

The intra-granular component preferably comprises from 0 to 1.5 percent by weight of croscarmellose sodium, based on the weight of the formulation.

When the second disintegrant is starch, the percent by weight of croscarmellose sodium in the formulation is preferably at least 3.0.

When the diluent is mannitol, the percent by weight of croscarmellose sodium in the formulation is preferably at least 2.0.

The formulation may further comprise a dye.

The formulation according to the invention may be prepared in a conventional manner.

Thus, the formulation may be prepared by mixing the ingredients, then compressing them into a tablet or filling them into a capsule. A tablet may then, if desired, be coated. It will be appreciated that the dissolution rate of a given formulation may decline if the tablet is compressed to an excessive hardness.

According to another aspect, therefore, the present invention provides a process for manufacturing a pharmaceutical formulation of tamoxifen citrate, which comprises formulating 5 to 15% by weight of tamoxifen citrate with a first disintegrant which is croscarmellose sodium, the percentage by weight of croscarmellose sodium present in the formulation being chosen such that, in six 20 mg unit doses, an average of at least 65 percent by weight of the tamoxifen citrate in the formulation will dissolve within 10 minutes in 1000 mL of 0.02N hydrochloric acid at 37° C. when stirred at 100 rpm.

The preferred formulation comprising an inter-granular component and an intra-granular component may be prepared by granulating together the ingredients of the inter-granular component, and then mixing the granulated material so obtained with the ingredients of the intra-granulating material. Conveniently, the ingredients of the inter-granular component are granulated using a solvent such as water. The resultant granules are then dried, for example using a fluid bed drier, and then passed through a screen, for example of 1270 micron. It has been found that the screen size and the form of the screen holes minimally influence the dissolution rate of the eventual tablet. The screened material is then blended with the ingredients of the intra-granular component, for example using a tumble blender, and the resultant mixture is pressed into a tablet mold or filled into a capsule. Optionally the tablet formulation is then provided with a non-performance aesthetic coating.

The following Examples illustrate the invention.

In each Example, the formulations were made following essentially the following procedure:

The ingredients of the inter-granular mixture were mixed with purified water in a Niro Fielder PP-1, High Shear Mixer with a Masterflex console Peristaltic Pump and Head, then dried in a Niro Fielder MP-1 fluid bed drier, measuring water content using a Computrac Moisture Analyzer, and milled using a Quadro comil, model 197S with screen 2A 050 G 037 19 136 (1270 micron). The resultant inter-granular mixture was then blended with the components of the intra-granular mixture using a P-K Twinshell Tumble Blender, and the resultant blend was compressed into tablets using a Key International DB-16 Rotary Press.

If desired, the tablet formulation may then be coated.

It will be appreciated that instead of compressing the formulation mixture into a tablet, it could have been filled into a capsule.

EXAMPLE 1

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline Cellulose NF | 25.0 | 10.00 |
| Croscarmellose Sodium NF | 5.0 | 2.00 |
| Povidone USP | 7.5 | 3.00 |
| Lactose Monohydrate NF | 150.2 | 60.09 |
| Intra-granular component |  |  |
| Microcrystalline Cellulose NF | 25.0 | 10.00 |
| Croscarmellose Sodium NF | 5.0 | 2.00 |
| Magnesium stearate | 1.9 | 0.75 |
| Total | 250.0 | 100.00 |

EXAMPLE 2

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline Cellulose NF | 25.0 | 10.00 |
| Croscarmellose Sodium NF | 5.0 | 2.00 |
| Povidone USP | 7.5 | 3.00 |
| Mannitol Granular, USP | 150.2 | 60.09 |
| Intra-granular component |  |  |
| Microcrystalline Cellulose NF | 25.0 | 10.00 |
| Croscarmellose Sodium NF | 5.0 | 2.00 |
| Magnesium stearate | 1.9 | 0.75 |
| Total | 250.0 | 100.00 |

EXAMPLE 3

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline Cellulose NF | 25.0 | 10.00 |
| Croscarmellose Sodium NF | 2.5 | 1.00 |
| Povidone USP | 7.5 | 3.00 |
| Lactose Monohydrate NF | 155.2 | 62.09 |
| Intra-granular component |  |  |
| Microcrystalline Cellulose NF | 25.0 | 10.00 |
| Croscarmellose Sodium NF | 2.5 | 1.00 |
| Magnesium stearate | 1.9 | 0.75 |
| Total | 250.0 | 100.00 |

EXAMPLE 4

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline Cellulose NF | 25.0 | 10.00 |
| Croscarmellose Sodium NF | 2.5 | 1.00 |
| Povidone USP | 7.5 | 3.00 |
| Lactose Monohydrate NF | 157.7 | 63.09 |
| Intra-granular component |  |  |
| Microcrystalline Cellulose NF | 25.0 | 10.00 |
| Croscarmellose Sodium NF | 0.0 | 0.00 |
| Magnesium stearate | 1.9 | 0.75 |
| Total | 250.0 | 100.00 |

EXAMPLE 5

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Corn Starch, NF | 25.0 | 10.00 |
| Croscarmellose Sodium NF | 2.5 | 1.00 |
| Povidone USP | 7.5 | 3.00 |
| Lactose Monohydrate NF | 157.7 | 63.09 |
| Intra-granular component |  |  |
| Corn Starch, NF | 20.0 | 8.00 |
| Croscarmellose Sodium NF | 5.0 | 2.00 |
| Magnesium stearate | 1.9 | 0.75 |
| Total | 250.0 | 100.00 |

EXAMPLE 6

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline cellulose, NF | 25.0 | 10.00 |
| Croscarmellose Sodium NF | 5.0 | 2.00 |
| Povidone USP | 7.5 | 3.00 |
| Mannitol Granular USP | 150.6 | 60.23 |
| Intra-granular component |  |  |
| Microcrystalline cellulose, NF | 25.0 | 10.00 |
| Croscarmellose Sodium NF | 3.8 | 1.50 |
| Magnesium stearate | 2.5 | 1.00 |
| Total | 250.0 | 100.00 |

EXAMPLE 7

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline cellulose, NF | 25.0 | 10.00 |
| Croscarmellose Sodium NF | 5.0 | 2.00 |
| Povidone USP | 5.0 | 2.00 |
| Mannitol Granular USP | 153.1 | 61.23 |
| Intra-granular component |  |  |
| Microcrystalline cellulose, NF | 25.0 | 10.00 |
| Croscarmellose Sodium NF | 3.8 | 1.50 |
| Magnesium stearate | 2.5 | 1.00 |
| Total | 250.0 | 100.00 |

EXAMPLE 8

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline cellulose, NF | 25.0 | 10.00 |
| Croscarmellose Sodium NF | 3.8 | 1.50 |
| Povidone USP | 7.5 | 3.00 |
| Mannitol Granular USP | 152.0 | 60.80 |
| Intra-granular component |  |  |
| Microcrystalline cellulose, NF | 25.0 | 10.00 |
| Croscarmellose Sodium NF | 3.8 | 1.50 |
| Magnesium stearate | 2.5 | 1.00 |
| Total | 250.0 | 100.00 |

EXAMPLE 9

250 mg Tablets Containing 20 mg Tamoxifen as Tamoxifen Citrate

|  | mg | w/w % |
|---|---|---|
| Inter-granular Component |  |  |
| Tamoxifen citrate | 30.40 | 12.16 |
| Microcrystalline cellulose, NF | 25.00 | 10.00 |
| Croscarmellose Sodium NF | 3.75 | 1.50 |
| Povidone USP | 10.00 | 4.00 |
| Mannitol Granular USP | 157.72 | 63.09 |
| Intra-granular component |  |  |
| Microcrystalline cellulose, NF | 20.00 | 8.00 |
| Croscarmellose Sodium NF | 1.25 | 0.50 |
| Magnesium stearate | 1.88 | 0.75 |
| Total | 250.00 | 100.00 |

Comparative Example 1

250 mg Tablets Containing 20 mg Tamoxifen as Tamoxifen Citrate

|  | mg | w/w % |
|---|---|---|
| Inter-granular Component |  |  |
| Tamoxifen citrate | 30.4 | 12.16 |
| Microcrystalline cellulose, NF | 25.0 | 10.00 |
| Croscarmellose Sodium NF | 2.5 | 1.00 |
| Povidone USP | 7.5 | 3.00 |
| Mannitol Granular USP | 153.3 | 61.34 |
| Intra-granular component |  |  |
| Microcrystalline cellulose, NF | 25.0 | 10.00 |
| Croscarmellose Sodium NF | 3.8 | 1.50 |
| Magnesium stearate | 2.5 | 1.00 |
| Total | 250.0 | 100.00 |

Measurement of UV Dissolution Profile for Tamoxifen Citrate Tablets

The dissolution rate of tablet formulations according to the present invention was measured in comparison to that of NOLVADEX® (United States material) and other tamoxifen citrate tablet formulations using the method described in the United States Pharmacopeia, USP 23, p 1478 (1998).

In the first stage of the method, 1000 mL of 0.02N hydrochloric acid is placed in each of six dissolution vessels and the temperature is allowed to equilibrate to 37.0±0.5° C. One tablet formulation is placed in each dissolution vessel and the contents of the vessel are stirred at 100 rpm. The contents of the vessel are sampled after stirring for 5, 10, 20, 30, and 45 minutes. The amount of tamoxifen that has dissolved in each sample is then determined by filtering the samples and then measuring UV absorption of the filtrate at a wavelength of about 275 nm in comparison with a reference standard, prepared by dissolving tamoxifen citrate RS in 0.02N hydrochloric acid.

The results of measuring the dissolution rates of the tablet formulations of Examples 1 to 9 of NOLVADEX®, and of Comparative Example 1 were as shown in Table 1 below:

TABLE 1

Dissolution ot Tamoxifen Citrate in Tablet Formulations
(Average of six tests)

| Formulation | Dissolution Time in Minutes ||||| 
|---|---|---|---|---|---|
|  | 5 | 10 | 20 | 30 | 45 |
| Example 1 | 92 | 99 | 101 | 98 | 99 |
| Example 2 | 71 | 90 | 95 | 98 | 102 |
| Example 3 | 74 | 89 | 93 | 96 | 97 |
| Example 4 | 75 | 85 | 92 | 94 | 98 |
| Example 5 | 59 | 81 | 90 | 95 | 99 |
| Example 6 | 50 | 72 | 88 | 93 | 95 |
| Example 7 | 73 | 82 | 91 | 93 | 94 |
| Example 8 | 55 | 76 | 91 | 95 | 96 |
| Example 9 | 11 | 66 | 95 | 97 | 98 |
| NOLVADEX® 20 mg | 12 | 35 | 74 | 87 | 94 |
| NOLVADEX® D 20 mg | 12 | 32 | 69 | 84 | 101 |
| Comparison 1 | 25 | 49 | 72 | 79 | 84 |

These results demonstrate that tablet formulations according to the present invention possess a substantially higher dissolution rate than NOLVADEX® 20 mg, NOLVADEX® D 20 mg or Comparison Example 1, which contains a reduced percentage by weight of croscarmellose sodium.

We claim:

1. A pharmaceutical formulation, which comprises from 5 to 15% by weight of tamoxifen citrate and a first disintegrant which is croscarmellose sodium, said formulation consisting of an inter-granular component and an intra-granular component, and said inter-granular component containing croscarmellose sodium and the tamoxifen citrate, the percentage by weight of croscarmellose sodium present in the formulation being selected in the way that, in six 20 mg unit doses, an average of at least 65 percent by weight of the tamoxifen citrate in the formulation will dissolve within 10 minutes in 1000 mL of 0.02N hydrochloric acid at 37° C. when stirred at 100 rpm.

2. A formulation as claimed in claim 1, which is in the form of a tablet.

3. A formulation as claimed in claim 1, in which the inter-granular component further comprises from 5 to 15% by weight of a second disintegrant, from 55 to 75% by weight of a diluent and from 0.5 to 5% by weight of a binder, based upon the weight of the formulation.

4. A formulation as claimed in claim 3, in which the second disintegrant is selected from the group consisting of starch and microcrystalline cellulose, the diluent is selected from the group consisting of lactose and mannitol, and the binder is selected from the group consisting of gelatin and polyvinylpyrrolidone.

5. A formulation as claimed in claim 4, in which the binder is polyvinylpyrrolidone.

6. A formulation as claimed in claim 5, in which the inter-granular component contains from 0.75 to 2.5 percent by weight of croscarmellose sodium, based on the weight of the formulation.

7. A formulation as claimed in claim 1, in which the intra-granular component comprises from 5 to 15% by weight of a third disintegrant and from 0.5 to 1.5% by weight of a lubricant, based upon the total weight of the formulation.

8. A formulation as claimed in claim 7, in which the third disintegrant is selected from the group consisting of starch and microcrystalline cellulose and the lubricant is magnesium stearate.

9. A formulation as claimed in claim 8, in which the intra-granular component comprises from 0 to 1.5 percent by weight of croscarmellose sodium, based on the weight of the formulation.

10. A formulation as claimed in claim 3, in which the second disintegrant is starch and the percent by weight of croscarmellose sodium in the formulation is at least 3.0.

11. A formulation as claimed in claim 3, in which the diluent is mannitol and the percent by weight of croscarmellose sodium in the formulation is at least 2.0.

12. A formulation as claimed in claim 1, in which the inter-granular component contains from 0.75 to 2.5 percent by weight of croscarmellose sodium, from 5 to 15% by weight of a second disintegrant selected from the group consisting of starch and microcrystalline cellulose, from 55 to 75% by weight of a diluent selected from the group consisting of lactose and mannitol and from 0.5 to 5% by weight of polyvinylpyrrolidone; and the intra-granular component contains from 0 to 1.5 percent by weight of croscarmellose sodium, from 5 to 15% by weight of a third disintegrant selected from the group consisting of starch and microcrystalline cellulose and from 0.5 to 1.5% by weight of magnesium stearate, based upon the weight of the formulation.

13. A process for manufacturing a pharmaceutical formulation of tamoxifen citrate, which comprises 5 to 15% by weight of tamoxifen citrate and a first disintegrant which is croscarmellose sodium, said formulation consisting of an inter-granular component and an intra-granular component, said inter-granular component containing the tamoxifen citrate and at least some of the croscarmellose sodium, the percentage by weight of croscarmellose sodium present in the formulation being that, in six 20 mg unit doses, an average of at least 65 percent by weight of the tamoxifen citrate in the formulation will dissolve within 10 minutes in 1000 mL of 0.02N hydrochloric acid at 37° C. when stirred at 100 rpm, wherein the ingredients of the inter-granular component are granulated together and then mixed with the ingredients of the intra-granular component.

14. A process as claimed in claim 13, wherein the inter-granular component contains from 0.75 to 2.5 percent by weight of croscarmellose sodium, from 5 to 15% by weight of a second disintegrant selected from the group consisting of starch and microcrystalline cellulose, from 55 to 75% by weight of a diluent selected from the group consisting of lactose and mannitol and from 0.5 to 5% by weight of polyvinylpyrrolidone; and the intra-granular component contains from 0 to 1.5 percent by weight of croscarmellose sodium, from 5 to 15% by weight of a third disintegrant selected from the group consisting of starch and microcrystalline cellulose and from 0.5 to 1.5% by weight of magnesium stearate, based upon the weight of the formulation.

* * * * *